United States Patent
Li et al.

(10) Patent No.: US 12,305,164 B2
(45) Date of Patent: May 20, 2025

(54) ESCHERICHIA COLI K-12 MG1655 BLBYZT6 AND APPLICATION THEREOF

(71) Applicant: Baolingbao Biology CO., LTD., Jinan (CN)

(72) Inventors: Kewen Li, Jinan (CN); Peigong Li, Jinan (CN); Qingmin Luan, Jinan (CN); Liujuan Kong, Jinan (CN); Xiaolan Xiong, Jinan (CN); Yaying Xue, Jinan (CN); Li Zhang, Jinan (CN); Shiying Yuan, Jinan (CN); Zhenzhen Li, Jinan (CN); Guilian Sun, Jinan (CN); Yuanliang Duan, Jinan (CN); Yunfei Li, Jinan (CN)

(73) Assignee: Baolingbao Biology CO., LTD., Jinan (CN)

( * ) Notice: Subject to any disclaimer, the term of this patent is extended or adjusted under 35 U.S.C. 154(b) by 0 days.

(21) Appl. No.: 18/426,195

(22) Filed: Jan. 29, 2024

(65) Prior Publication Data

US 2025/0122466 A1     Apr. 17, 2025

(30) Foreign Application Priority Data

Oct. 17, 2023   (CN) .......................... 202311336921.0

(51) Int. Cl.
*C12N 1/20* (2006.01)
*C12P 19/00* (2006.01)
*C12R 1/19* (2006.01)

(52) U.S. Cl.
CPC .............. *C12N 1/205* (2021.05); *C12P 19/00* (2013.01); *C12R 2001/19* (2021.05)

(58) Field of Classification Search
CPC ...... C12N 1/205; C12P 19/00; C12R 2001/19
See application file for complete search history.

(56) References Cited

U.S. PATENT DOCUMENTS

2016/0333042 A1   11/2016   Jennewein

FOREIGN PATENT DOCUMENTS

| | | |
|---|---|---|
| CN | 105814070 A | 7/2016 |
| CN | 111218488 A | 6/2020 |
| CN | 111575220 A | 8/2020 |
| CN | 112662715 A | 4/2021 |
| CN | 112920234 A | 6/2021 |
| CN | 114032261 A | 2/2022 |
| CN | 114774343 A | 7/2022 |
| CN | 114874964 A | 8/2022 |
| CN | 116769808 A | 9/2023 |
| KR | 20230094102 A | 6/2023 |
| WO | 2022136337 A2 | 6/2022 |

OTHER PUBLICATIONS

Hyun-Jae Lee et al., "Simultaneous production of 2'-fucosyllactose and difucosyllactose by engineered *Escherichia coli* with high secretion efficiency", Biotechnol. J., vol. 17, No. 3, Dec. 31, 2022, entire document.

*Primary Examiner* — Louise W Humphrey
*Assistant Examiner* — Rachel Emily Martin

(57) ABSTRACT

The invention relates to the technical field of breast milk oligosaccharide production, and particularly to an *Escherichia coli* K-12 MG1655 BLBYZT6 and an application thereof. The *Escherichia coli* K-12 MG1655 BLBYZT6 is preserved in the China General Microbiological Culture Collection Center, with the collection number of CGMCC No. 28317, the collection date of Aug. 31, 2023, and the collection institution address of No. 3, Yard 1, Beichen West Road, Chaoyang District, Beijing. The *Escherichia coli* K-12 MG1655 BLBYZT6 of the invention is applied in fermentation production of 2'-fucosyllactose and difucosyllactose. The invention improves a yield of the 2'-fucosyllactose, reduces a dry matter proportion of a non-target product, realizes simple separation and purification, is beneficial for industrial production, and can co-produce the difucosyllactose with a purity greater than 90% at the same time.

9 Claims, No Drawings

ESCHERICHIA COLI K-12 MG1655 BLBYZT6 AND APPLICATION THEREOF

CROSS REFERENCE TO RELATED APPLICATIONS

This application claims foreign priority of Chinese Patent Application No. 202311336921.0, filed on Oct. 17, 2023 in the China National Intellectual Property Administration, the disclosures of all of which are hereby incorporated by reference.

TECHNICAL FIELD

The present invention relates to the technical field of breast milk oligosaccharide production, and particularly to an *Escherichia coli* K-12 MG1655 BLBYZT6 and an application thereof.

BACKGROUND OF THE PRESENT INVENTION

2'-fucosyllactose (2'-FL) is composed of D-glucose, D-galactose and L-fucose, is the most abundant oligosaccharide in human milk oligosaccharide, has a concentration of about 2 g/L to 5 g/L in human milk, and accounts for about 30% of total human milk oligosaccharide detected. The human milk oligosaccharide is an indispensable ingredient in infant development, is conductive to the growth of probiotics such as Bifidobacterium, Lactobacillus and Bacteroides in infant intestinal tract, and is conductive to the prevention of infection with pathogenic bacteria, the regulation of immune system, the promotion of early development of infant brain, and other functions.

The 2'-FL has been widely used in infant formula, dairy products and special-purpose foods abroad. At present, researches on the 2'-FL at home and abroad mainly focus on the construction of bacterial strains for producing the 2'-FL by microbial fermentation, for example:

CN114774343A discloses an *Escherichia coli* engineering strain for producing 2'-fucosyllactose and an application thereof, wherein a series of genes related to substrate degradation and intermediate product shunting in *Escherichia coli* are knocked out through a CRISPR/Cas9 gene editing system, different enzymes are subjected to genome overexpression or plasmid overexpression regulation and control, and the finally constructed *Escherichia coli* engineering strain can produce the 2'-fucosyllactose under a condition of a 3-L fermentation tank with a fermentation yield of 57.7 g/L.

CN114032261A discloses a method for obtaining high-purity fucosyllactose by degrading lactose in a fermentation broth, wherein membrane treatment is carried out for a total of three times to remove bacteria and varied saccharides, and a feed liquid is diluted with water 4 to 6 times the weight of the feed liquid in a membrane filtration process; in a treatment process, in order to reduce a content of lactose, lactase is added to degrade the lactose; and an electric conductance of a concentrated solution intercepted by ion-exchange desalination treatment is lower than 400 us/cm, and a purity of finally prepared 2'-fucosyllactose is not lower than 95%.

CN105814070A discloses a method for chromatographic purification of a neutral human milk oligosaccharide by a simulated moving bed, wherein a fermentation extracting solution containing the human milk oligosaccharide is subjected to chromatographic separation for one or more times by a chromatographic column of the simulated moving bed, and then is spray-dried to obtain 2'-fucosyllactose with a purity greater than 92%.

CN202110115032.6 discloses an enrichment and purification method of 2'-fucosyllactose, wherein the purification comprises steps of filtering a fermentation broth, concentrating the fermentation broth at a low temperature under an increased pressure, precipitating with absolute alcohol and centrifuging to remove protein, concentrating at a low temperature under a low pressure, pretreating by an activated carbon chromatography column, subjecting 2'-fucosyllactose to chromatographic purification, concentrating at a low temperature under a reduced pressure, and freeze-drying to obtain a finished product, and a chromatographic purity of the finished product is 85.04%.

The defects of the above patents lie in a low conversion rate and a high dry matter proportion of a non-target saccharide, which are not conducive to separation and purification; and meanwhile, there are few researches on the separation and purification of the 2'-FL fermentation broth, a process route is long, and equipment is complicated.

Difucosyllactose (DFL) is an oligosaccharide existing in a 2'-fucosyllactose product, has a low content and various biological activities, comprises a prebiotic effect, an anti-adhesion performance and an immunomodulation function, and may be used as a standard human milk oligosaccharide product. In the prior art, the difucosyllactose is generally prepared by a synthetic method, with a low yield and a product purification difficulty, and in the prior art, there is no report on the co-production of the difucosyllactose by the fermentation production of the 2'-fucosyllactose.

SUMMARY OF THE PRESENT INVENTION

Aiming at the problems of a low conversion rate, a long process flow and the like in the prior art, the present invention provides an *Escherichia coli* K-12 MG1655 BLBYZT6 and an application thereof, which improves a yield of 2'-fucosyllactose, reduces a dry matter proportion of a non-target product, realizes simple separation and purification flows, is more beneficial for industrial production, and can co-produce difucosyllactose (DFL) with a purity greater than 90% at the same time.

In a first aspect, the present invention provides an *Escherichia coli* K-12 MG1655 BLBYZT6, wherein the *Escherichia coli* K-12 MG1655 BLBYZT6 is preserved in the China General Microbiological Culture Collection Center, with the collection number of CGMCC No. 28317, the collection date of Aug. 31, 2023, and the collection institution address of No. 3, Yard 1, Beichen West Road, Chaoyang District, Beijing. It is well known in the art that the *Escherichia coli*, also known as *E. coli*, was discovered by Escherich in 1885.

Further, a culture method of the *Escherichia coli* K-12 MG1655 BLBYZT6 comprises: inoculating a bacterial strain to a seed solution culture medium, and fermenting and culturing the bacterial strain at a temperature of 36° C. to 38° C. under a stirring rate of 150 r/min to 250 r/min for 5 hours to 10 hours; the seed solution culture medium is prepared from ingredients at the following concentrations: 8 g/L to 14 g/L compound peptone, 4 g/L to 12 g/L yeast powder and 8 g/L to 12 g/L sodium chloride; and the compound peptone comprises tryptone and bovine bone peptone in a weight ratio of 2 to 3:1.

In a second aspect, the present invention provides an application of the *Escherichia coli* K-12 MG1655

BLBYZT6, which refers to an application in fermentation production of 2'-fucosyllactose and difucosyllactose.

Further, a method for the fermentation production of the 2'-fucosyllactose and the difucosyllactose comprises the following steps of:
(1) inoculating the *Escherichia coli* K-12 MG1655 BLBYZT6 to a seed solution culture medium to obtain a seed solution;
(2) inoculating the seed solution to a fermentation culture medium for fermentation to obtain a fermentation broth; and
(3) subjecting the fermentation broth to membrane filtration, concentration, crystallization with acetic acid and centrifugation, then drying a solid to obtain a 2'-fucosyllactose crystal, and subjecting an acetic acid crystal separation solution to decolorization, ion-exchange, concentration, chromatographic separation and drying to obtain the difucosyllactose.

Further, in the step (2), the fermentation culture medium is prepared from ingredients at the following concentrations: 5 g/L to 40 g/L glucose, 5 g/L to 40 g/L lactose, 10 g/L to 15 g/L compound peptone, 20 g/L to 30 g/L yeast powder, 10 g/L to 20 g/L dipotassium hydrogen phosphate, 1 g/L to 5 g/L potassium dihydrogen phosphate and 5 ml/L to 15 ml/L trace metal element; and the trace metal element comprises ingredients at the following concentrations: 6 g/L ferrous sulfate, 0.35 g/L manganese sulfate monohydrate, 2.2 g/L zinc sulfate heptahydrate, 1.0 g/L anhydrous copper sulfate and 0.11 g/L ammonium molybdate.

Further, in the step (2), technological conditions of fermentation are as follows: firstly, a fermentation temperature is adjusted to be 36° C. to 38° C., a fermentation pressure is adjusted to be 0.03 MPa to 0.04 MPa, a fermentation pH value is adjusted to be 6.8 to 7.0, and fermentation time is adjusted to be 8 hours to 10 hours; then, the fermentation temperature is adjusted to be 28° C. to 32° C., the fermentation pressure is adjusted to be 0.05 MPa to 0.08 MPa, the fermentation pH value is adjusted to be 7.2 to 7.6, and the peptone, the lactose and the glucose are added in a fermentation process; and the whole fermentation lasts for 100 hours to 130 hours at a stirring rate of 150 r/min to 300 r/min.

Further, in the step (3), the concentration is carried out at a temperature lower than or equal to 70° C., and the fermentation broth is concentrated until a content of the solid is greater than 83%.

Further, in the step (3), the crystallization with acetic acid is carried out at a constant temperature of 50° C., an addition amount of the acetic acid is 0.5 to 3 times of a mass of a feed liquid, and the crystallization lasts for 30 hours to 50 hours.

Further, in the step (3), the solid after centrifugation is subjected to dissolution, decolorization, ion-exchange, concentration and drying to obtain 2'-fucosyllactose powder, the ion-exchange adopts full-bed ion-exchange with mixed cation and anion resins, and the cation resin and the anion resin are a D001 resin and a D301-F resin in a volume ratio of 100:110. The D001 resin is a cation strong acid resin, and the D301-F resin is an anion weak alkali resin, which can avoid an influence of over-acid and over-alkali on the feed liquid, thus maintaining a stability of the feed liquid.

Further, in the step (3), the decolorization adopts activated carbon decolorization, an amount of activated carbon is 3% to 5% of a dry matter content of the feed liquid, the decolorization is carried out at a temperature of 50° C. to 60° C. and lasts for 50 minutes to 70 minutes, and a light transmittance of the feed liquid is greater than 85%; as for conditions of the ion-exchange, a feed temperature is 30° C. to 40° C., a flow speed is 2 Bv/h to 3 Bv/h, a discharge conductance is lower than 50 us/cm, and a discharge pH value is 3 to 6; the concentration is carried out at a temperature of 60° C. to 67° C. until the content of the solid is 50%; and as for conditions of the chromatographic separation, a mass concentration of chromatographic feed is 50%, a temperature is 60° C. to 63° C., and a ratio of water to material is 1: (3 to 3.5).

The present invention has the beneficial effects as follows:
(1) according to the present invention, the 2'-fucosyllactose is produced by efficiently fermenting the *Escherichia coli* K-12 MG1655 BLBYZT6 bacterial strain, the fermentation process has two stages, and comprises temperature change, pressure change and pH value regulation and control, wherein in the first stage of fermentation, the temperature, the pressure and the pH value are the most suitable conditions for bacterial growth, thus being beneficial for rapid bacterial growth; and in the second stage of fermentation, the temperature is reduced to an optimal reaction temperature of the bacterial strain, the pressure and the pH value are adjusted at the same time, and nitrogen and carbon sources are added, so that production of a target reaction product is improved, a dry matter area proportion of a by-product is reduced, and a post-extraction difficulty is reduced.
(2) according to the present invention, the 2'-fucosyllactose crystal with a purity greater than 96% is obtained by subjecting the fermentation broth to concentration, crystallization with acetic acid and centrifugation, and meanwhile, according to the present invention, the high-quality 2'-fucosyllactose powder may be obtained by further refining, which shortens a post-extraction process route.
(3) according to the present invention, the acetic acid is used instead of water in the prior art for crystallization in the concentrated fermentation broth, which can realize a primary crystallization yield greater than 65% of the 2'-fucosyllactose.
(4) according to the present invention, the separation liquid after crystallization and centrifugation is purified, which realizes the co-production of the difucosyllactose (DFL) with a purity greater than 90%.

DETAILED DESCRIPTION OF PREFERRED EMBODIMENTS

In order to make those skilled in the art better understand technical solutions of the present invention, the technical solutions in embodiments of the present invention are clearly and completely described hereinafter. Obviously, the described embodiments are merely some but not all of the embodiments of the present invention. Based on the embodiments in the present invention, all other embodiments obtained by those of ordinary skills in the art without going through any creative work should fall within the scope of protection of the present invention.

An *Escherichia coli* K-12 MG1655 BLBYZT6 used in the present invention is obtained by the following method.

An *Escherichia coli* K-12 MG1655 bacterial strain purchased by the applicant is used in the present invention, and a donor source of α-1, 2-fucosyl transferase in the *Escherichia coli* K-12 MG1655 bacterial strain is *Helicobacter* spp.

As for the *Escherichia coli* K-12 MG1655 BLBYZT6 used in the present invention, the *Escherichia coli* K-12 MG1655 bacterial strain preserved by the applicant is subjected to compound mutation treatment of ultraviolet ray and nitrosoguanidine, and an excellent high-yield bacterial strain is obtained by determining a conversion rate of 2'-fucosyllactose produced, which specifically comprises the following steps.

(1) Ultraviolet ray mutation: *Escherichia coli* K-12 MG1655 is picked by an inoculating loop for slant culture in a triangular flask filled with sterile water, and then placed on a magnetic stirrer to shake for 1 hour. A suspension is poured into a sterile plate containing a sterile pin. The plate is uncovered to be irradiated at a place 28.5 cm under a preheated 25 W ultraviolet lamp for 0 second, 20 seconds, 40 seconds, 60 seconds, 80 seconds, 100 seconds and 120 seconds, and bacterial liquids with different irradiation doses are diluted to $10^{-1}$, and placed in the dark for 1 hour. Then, the bacterial liquids are respectively diluted to $10^{-3}$ with normal saline, 0.1 ml of diluted bacterial liquid is sucked and coated on a culture medium plate, and 3 plates are coated with the diluted bacterial liquid at each dilution. The coated plate is wrapped in black cloth, and cultured in a biochemical incubator at 37° C. for about 5 days until mature bacterial colonies grew, and bacterial strains with a lethal rate greater than 80% after the ultraviolet ray mutation are selected for screening to obtain an excellent bacterial strain YZTUV-28.

(2) Nitroguanidine mutation: the bacterial strain YZTUV-28 is subjected to nitrosoguanidine mutation treatment. An activated bacterial strain YZTUV-28 is taken for slant culture, and placed in a triangular flask to shake for 2 hours, 10 ml of prepared suspension is taken, added with 0.2 mL of 0.5% nitrosoguanidine, mixed evenly, and then placed in a constant-temperature shaking box to shake at 37° C. for 10 minutes, 20 minutes, 30 minutes, 40 minutes, 50 minutes, 60 minutes and 70 minutes respectively, and after the reaction is finished, 0.1 mol/L sodium hydroxide is immediately added to adjust a pH value, so as to terminate the reaction. Meanwhile, a group without nitrosoguanidine is used as a control group. Control and mutated bacterial liquids are diluted with a phosphate buffer. The bacterial liquids are respectively sucked and coated on a culture medium plate, then placed in a biochemical incubator at 37° C. for about 5 days until mature bacterial colonies grow, mortality rates are counted, and single bacterial colonies are randomly selected from the plate.

(3) Screening: the bacterial colonies in the plate are selected for shake-flask culture, a conversion yield of 2'-fucosyllactose is determined, and a bacterial strain with a high conversion rate is screened out to be numbered as K-12 MG1655 BLBYZT6.

The bacterial strain screened out is entrusted to China Center of Industrial Culture Collection for microbial identification, with an identification report number of 22-0607-01342.01-03129.

Culture method: the culture is carried out with a TSA culture medium at 37° C. for 18 hours.

Macroscopic morphology: the bacterial colonies have a light yellow color, a round shape, a wet surface, non-transparency, and a neat edge.

Microscopic morphology: the bacteria are rod-shaped, have a size of (0.4–0.6) μm×(0.9–2.1) μm, are arranged singly or in pairs, and are Gram-negative.

Physiological and biochemical experimental results of the bacterial strain screened out are shown in Table 1.

TABLE 1

| Physiological and biochemical detection results of bacterial strain | | | | | | | |
|---|---|---|---|---|---|---|---|
| Alanine-phenylalanine-proline arylamidase | − | Adonitol | − | L-pyrrolidinylarylamidase | − | L-arabitol | − |
| D-cellobiose | − | β-galactosidase | + | Production of $H_2S$ | − | β-N-acetylaminoglucosidase | − |
| Glutaminase pNA | − | D-glucose | + | γ-glutamyltransferase | − | Fermentation of glucose | + |
| β-glucosidase | − | D-maltose | + | D-mannitol | + | D-mannose | + |
| β-xylosidase | − | β-alanine arylamidase pNA | − | L-proline arylamidase | + | Lipase | − |
| Gulose | − | Tyrosine arylaminase | + | Urease | − | D-sorbitol | + |
| Sucrose | − | D-tagatose | − | D-trehalose | + | Citrate (sodium citrate) | − |
| Malonate | − | 5-keto-gluconate | + | Alkali production with lactate | + | α-glucosidase | − |
| Alkali production with succinate | + | β-N-acetylgal actosidase | − | α-galactosidase | + | Phosphatase | + |
| Glycine arylamidase | + | Ornithine decarboxylase | − | Lysine decarboxylase | + | Assimilation of histidine | − |
| Coumaric acid | + | β-glucuronidase | − | 0/129 drug resistance | + | Glutamate-glycine-arginine arylamidase | − |
| Assimilation of L-malate | − | ELLMAN reagent | + | Assimilation of L-lactate | − | | |

In the table, "+" refers to being positive and "−" refers to being negative.

By the identification of China Center of Industrial Culture Collection, the bacterial strain K-12 MG1655 BLBYZT6 screened out by the present invention is identified as *Escherichia coli* and named as *Escherichia coli* K-12 MG1655 BLBYZT6.

Embodiment 1

A method for fermentation production of 2'-fucosyllactose by using *Escherichia coli* K-12 MG1655 BLBYZT6 specifically comprised that following steps.

(1) The *Escherichia coli* K-12 MG1655 BLBYZT6 was inoculated to a seed solution culture medium to obtain a seed solution. The seed solution culture medium comprised: 8 g/L compound peptone (composed of tryptone and bovine bone peptone in a weight ratio of 3:1), 12 g/L yeast powder and 8 g/L sodium chloride. A culture method comprised fermenting and culturing the bacterial strain at a temperature of 37° C. under a stirring rate of 150 r/min for 10 hours.

(2) The seed solution was inoculated to a fermentation culture medium for fermentation to obtain a fermentation broth. The fermentation culture medium comprised 20 g/L glucose, 40 g/L lactose, 15 g/L compound peptone (composed of tryptone and bovine bone peptone in a weight ratio of 3:1), 30 g/L yeast powder, 20 g/L dipotassium hydrogen phosphate, 5 g/L potassium dihydrogen phosphate and 15 ml/L trace metal element. The trace metal element comprised 6 g/L ferrous sulfate, 0.35 g/L manganese sulfate monohydrate, 2.2 g/L zinc sulfate heptahydrate, 1.0 g/L anhydrous copper sulfate and 0.11 g/L ammonium molybdate. The seed solution was inoculated to the fermentation culture medium by 10% inoculation amount. Technological conditions of fermentation were as follows: firstly, a fermentation temperature was adjusted to be 36° C. to 38° C., a fermentation pressure was adjusted to be 0.03 MPa to 0.04 MPa, a fermentation pH value was adjusted to be 6.8 to 7.0, and fermentation time was adjusted to be 8 hours to 10 hours; then, the fermentation temperature was adjusted to be 28° C. to 32° C., the fermentation pressure was adjusted to be 0.05 MPa to 0.08 MPa, the fermentation pH value was adjusted to be 7.2 to 7.6, and the peptone, the lactose and the glucose were added in a fermentation process; and the whole fermentation lasted for 120 hours at a stirring rate of 200 r/min.

(3) The fermentation broth obtained in the step (2) was filtered by a membrane and then a sterile fermentation broth was collected, the sterile fermentation broth was concentrated at a temperature lower than or equal to 70° C., and the sterile fermentation broth was concentrated until a content of a solid was greater than 83%. The concentrated solution was added with acetic acid twice a mass of a feed liquid to be crystallized at a constant temperature of 50° C. for 40 hours. After centrifugation, the solid was dried to obtain a 2'-fucosyllactose crystal product with a purity greater than 96%.

(4) The solid crystal crude product obtained after centrifugation in the step (3) was dissolved and then decolorized by using activated carbon. A decolorized feed liquid was ion-exchanged by a mixed ion exchanger to reduce an electric conductivity, and resins of the mixed ion exchanger comprised a strong acid D001 resin and a weak alkali D301-F resin in a weight ratio of 100:110. An ion-exchanged discharge was concentrated by an evaporator until a content of a solid was 60%, and the concentrated solution was dried at a drying temperature of 135° C. to 165° C. and an exhaust temperature of 65° C. to 105° C. under a negative pressure of $-1.0 \times 100$ Pa. After drying, a high-quality 2'-fucosyllactose powder product was obtained.

Embodiment 2

A method for fermentation production of 2'-fucosyllactose by using *Escherichia coli* K-12 MG1655 BLBYZT6 specifically comprised that following steps.

(1) The *Escherichia coli* K-12 MG1655 BLBYZT6 was inoculated to a seed solution culture medium to obtain a seed solution. The seed solution culture medium comprised: 8 g/L compound peptone (composed of tryptone and bovine bone peptone in a weight ratio of 2:1), 8 g/L yeast powder and 8 g/L sodium chloride. A culture method comprised fermenting and culturing the bacterial strain at a temperature of 37° C. under a stirring rate of 250 r/min for 5 hours.

(2) The seed solution was inoculated to a fermentation culture medium for fermentation to obtain a fermentation broth. The fermentation culture medium comprised 40 g/L glucose, 40 g/L lactose, 10 g/L compound peptone (composed of tryptone and bovine bone peptone in a weight ratio of 3:1), 25 g/L yeast powder, 15 g/L dipotassium hydrogen phosphate, 1 g/L potassium dihydrogen phosphate and 10 ml/L trace metal element. The trace metal element comprised 6 g/L ferrous sulfate, 0.35 g/L manganese sulfate monohydrate, 2.2 g/L zinc sulfate heptahydrate, 1.0 g/L anhydrous copper sulfate and 0.11 g/L ammonium molybdate. The seed solution was inoculated to the fermentation culture medium by 6% inoculation amount. Technological conditions of fermentation were as follows: firstly, a fermentation temperature was adjusted to be 36° C. to 38° C., a fermentation pressure was adjusted to be 0.03 MPa to 0.04 MPa, a fermentation pH value was adjusted to be 6.8 to 7.0, and fermentation time was adjusted to be 8 hours to 10 hours; then, the fermentation temperature was adjusted to be 28° C. to 32° C., the fermentation pressure was adjusted to be 0.05 MPa to 0.08 MPa, the fermentation pH value was adjusted to be 7.2 to 7.6, and the peptone, the lactose and the glucose were added in a fermentation process; and the whole fermentation lasted for 100 hours at a stirring rate of 150 r/min.

(3) The fermentation broth obtained in the step (2) was filtered by a membrane and then a sterile fermentation broth was collected, the sterile fermentation broth was concentrated at a temperature lower than or equal to 70° C., and the sterile fermentation broth was concentrated until a content of a solid was greater than 83%. The concentrated solution was added with acetic acid 0.5 times a mass of a feed liquid to be crystallized at a constant temperature of 50° C. for 30 hours. After centrifugation, the solid was dried to obtain a 2'-fucosyllactose crystal product with a purity greater than 96%.

(4) The solid crystal crude product obtained after centrifugation in the step (3) was dissolved and then decolorized by using activated carbon. A decolorized feed liquid was ion-exchanged by a mixed ion exchanger to reduce an electric conductivity, and resins of the mixed ion exchanger comprised a strong acid D001 resin and a weak alkali D301-F resin in a weight ratio of 100:110. An ion-exchanged discharge was concentrated by an evaporator until a content of a solid was 55%, and the concentrated solution was dried at a drying temperature of 135° C. to 165° C. and an exhaust temperature of 65° C. to 105° C. under a negative pressure of $-1.0 \times 100$ Pa. After drying, a high-quality 2'-fucosyllactose powder product was obtained.

Embodiment 3

A method for fermentation production of 2'-fucosyllactose by using *Escherichia coli* K-12 MG1655 BLBYZT6 specifically comprised that following steps.

(1) The *Escherichia coli* K-12 MG1655 BLBYZT6 was inoculated to a seed solution culture medium to obtain a seed solution. The seed solution culture medium comprised: 14 g/L compound peptone (composed of tryptone and bovine bone peptone in a weight ratio of 2:1), 4 g/L yeast powder and 12 g/L sodium chloride. A culture method comprised fermenting and culturing the bacterial strain at a temperature of 37° C. under a stirring rate of 200 r/min for 7 hours.

(2) The seed solution was inoculated to a fermentation culture medium for fermentation to obtain a fermentation broth. The fermentation culture medium comprised 5 g/L glucose, 5 g/L lactose, 15 g/L compound peptone (composed of tryptone and bovine bone peptone in a weight ratio of 3:1), 20 g/L yeast powder, 10 g/L dipotassium hydrogen phosphate, 4 g/L potassium dihydrogen phosphate and 5 ml/L trace metal element. The trace metal element comprised 6 g/L ferrous sulfate, 0.35 g/L manganese sulfate monohydrate, 2.2 g/L zinc sulfate heptahydrate, 1.0 g/L anhydrous copper sulfate and 0.11 g/L ammonium molybdate. The seed solution was inoculated to the fermentation culture medium by 8% inoculation amount. Technological conditions of fermentation were as follows: firstly, a fermentation temperature was adjusted to be 36° C. to 38° C., a fermentation pressure was adjusted to be 0.03 MPa to 0.04 MPa, a fermentation pH value was adjusted to be 6.8 to 7.0, and fermentation time was adjusted to be 8 hours to 10 hours; then, the fermentation temperature was adjusted to be 28° C. to 32° C., the fermentation pressure was adjusted to be 0.05 MPa to 0.08 MPa, the fermentation pH value was adjusted to be 7.2 to 7.6, and the peptone, the lactose and the glucose were added in a fermentation process; and the whole fermentation lasted for 130 hours at a stirring rate of 300 r/min.

(3) The fermentation broth obtained in the step (2) was filtered by a membrane and then a sterile fermentation broth was collected, the sterile fermentation broth was concentrated at a temperature lower than or equal to 70° C., and the sterile fermentation broth was concentrated until a content of a solid was greater than 83%. The concentrated solution was added with acetic acid 3 times a mass of a feed liquid to be crystallized at a constant temperature of 50° C. for 50 hours. After centrifugation, the solid was dried to obtain a 2'-fucosyllactose crystal product with a purity greater than 96%.

(4) The solid crystal crude product obtained after centrifugation in the step (3) was dissolved and then decolorized by using activated carbon. A decolorized feed liquid was ion-exchanged by a mixed ion exchanger to reduce an electric conductivity, and resins of the mixed ion exchanger comprised a strong acid D001 resin and a weak alkali D301-F resin in a weight ratio of 100:110. An ion-exchanged discharge was concentrated by an evaporator until a content of a solid was 65%, and the concentrated solution was dried at a drying temperature of 135° C. to 165° C. and an exhaust temperature of 65° C. to 105° C. under a negative pressure of $-1.0 \times 100$ Pa. After drying, a high-quality 2'-fucosyllactose powder product was obtained.

Embodiment 4

The acetic acid crystal separation solution in the step (3) in Embodiments 1 to 3 was taken, added with activated carbon in an amount of 3% to 5% of a dry matter content to be decolorized at 55° C. to 60° C. for 50 minutes to 70 minutes, and then filtered and ion-exchanged. As for conditions of the ion-exchange, a feed temperature was 30° C. to 40° C., and an ion-exchange flow speed was 2 Bv/h to 3 Bv/h (according to a resin volume). The feed liquid was concentrated at 60° C. to 67° C. until a content of a solid was 50%, and difucosyllactose was subjected to chromatographic purification. As for conditions of the chromatographic separation, a mass concentration of chromatographic feed was 50%, a temperature was 60° C. to 63° C., and a ratio of water to material was 1:(3 to 3.5). The purified difucosyllactose was dried to obtain high-purity difucosyllactose with a purity of 91.34%.

Comparative Example 1

Different from Embodiment 1, the peptone of the seed solution and the fermentation culture medium was tryptone.

Comparative Example 2

Different from Embodiment 1, in the step (3), technological conditions of fermentation were as follows: the fermentation temperature was 36° C. to 38° C., the fermentation pressure was 0.05 MPa to 0.08 MPa, and the fermentation pH value was 6.8 to 7.0. The peptone, the lactose and the glucose were added in the fermentation process. The fermentation culture was carried out at 150 r/min to 300 r/min for 110 hours to 140 hours to obtain the fermentation broth.

Comparative Example 3

Different from Embodiment 1, in the step (3), a crystallization method of the concentrated solution was as follows: the concentrated solution was cooled to 50° C. at a rate of 2° C./h, added with a seed crystal in an amount of 0.08% of a crystal mass, and then cooled to 20° C. at a rate of 1° C./h, and the crystal was centrifugally dried after heat preservation at 20° C. for 15 hours.

Experimental Example 1

1 mL of 2'-fucosyllactose fermentation broths prepared in Embodiments 1 to 3 and Comparative Examples 1 to 3 were taken respectively and centrifuged at 10,000 rpm for 10 minutes, supernatants were taken for HPLC determination, area proportions of various ingredients in the fermentation broths were recorded, and fermentation yields of 2'-FL were calculated according to determination results. Results were shown in Table 2 below. HPLC detection conditions comprised: a high performance liquid chromatography (HPLC) system (Waters E 2695); a chromatographic column: Carbohydrate Analysis (SHODEX Sugar SH 1011); a detector: differential detector; a mobile phase: 0.5 mmol/L $H_2SO_4$; a flow rate: 0.6 mL/min; a column temperature: 60° C.; and a sample volume: 20 μL.

Experimental Example 2

Masses of the crystallized feed liquids in Embodiments 1 to 3 and Comparative Example 4 before and after centrifugation were recorded, moisture contents of the crystals after crystallization were determined, and then crystallization yields were calculated. Purities of the crystals after centrifugation were determined by HPLC, with HPLC detection conditions the same as those in Embodiment 1. Results were shown in Table 3 below.

TABLE 2

Dry matter area proportions of 2'-FL and other saccharides in fermentation broths and fermentation yield data of 2'-FL in Embodiments 1 to 3 and Comparative Examples 1 to 2

| Item | Fermentation yield of 2'-FL g/L | Dry matter area proportion of 2'-FL in fermentation broth % | Dry matter area proportion of other saccharides in fermentation broth % |
|---|---|---|---|
| Embodiment 1 | 77.72 | 82.33 | 17.67 |
| Embodiment 2 | 75.89 | 80.00 | 20.00 |
| Embodiment 3 | 76.11 | 81.59 | 18.41 |
| Comparative Example 1 | 60.68 | 69.41 | 30.59 |
| Comparative Example 2 | 44.98 | 61.4 | 38.6 |

TABLE 3

Crystal yields and crystal purities of 2'-FL
obtained in Embodiments 1 to 3 and Comparative Example 3

| Item | Crystal yield of 2'-FL | Crystal purity of 2'-FL | Crystal size of 2'-FL | |
|---|---|---|---|---|
| | | | 0.15 mm to 0.18 mm | <0.15 mm |
| Embodiment 1 | 69.34% | 97.53% | 71.21% | 23.44% |
| Embodiment 2 | 65.56% | 96.98% | 69.88% | 28.67% |
| Embodiment 3 | 67.40% | 97.14% | 73.41% | 21.90% |
| Comparative Example 3 | 36.78% | 83.14% | 0% | 100% |

The present invention is described in detail through preferred embodiments, but the present invention is not limited to the embodiments. Ordinary skills in the art can make various equivalent modifications or substitutions to the embodiments of the present invention without departing from the spirit and essence of the present invention, and these modifications or substitutions should be within the scope of the present invention/the technical scope disclosed in the present invention by those skilled in the art. It is easy to think that the changes or substitutions are all within the scope of protection of the present invention.

We claim:

1. An *Escherichia coli* K-12 MG1655 BLBYZT6, wherein the *Escherichia coli* K-12 MG1655 BLBYZT6 is preserved in the China General Microbiological Culture Collection Center, with the collection number of CGMCC No. 28317.

2. A method of culturing the *Escherichia coli* K-12 MG1655 BLBYZT6 according to claim 1, comprising:
inoculating the bacterial strain to a seed culture medium; and
culturing the bacterial strain at a temperature of 36° C. to 38° C. at a stirring rate of 150 to 250 r/min for 5 to 10 hours,
wherein the seed culture medium comprises 4 to 12 g/L yeast powder, 8 to 12 g/L sodium chloride, and 8 to 14 g/L compound peptone,
wherein the compound peptone comprises tryptone and bovine bone peptone in a weight ratio of 2:1 to 3:1.

3. A method for preparing 2'-fucosyllactose and difucosyllactose, comprising the steps of:
(1) inoculating the *Escherichia coli* K-12 MG1655 BLBYZT6 according to claim 1 to a seed culture medium to obtain a seed solution;
(2) inoculating the seed solution to a fermentation culture medium to obtain a fermentation broth; and
(3) subjecting the fermentation broth to membrane filtration, concentration, crystallization with acetic acid and centrifugation to obtain a solid, then drying the solid to obtain a 2'- fucosyllactose crystal, wherein a supernatant is obtained from the centrifugation, as an acetic acid crystal separation solution; subjecting the acetic acid crystal separation solution to decolorization, ion-exchange, concentration, chromatographic separation and drying to obtain the difucosyllactose.

4. The method according to claim 3, wherein, in step (2), the fermentation culture medium comprises: 5 to 40 g/L glucose, 5 to 40 g/L lactose, 10 to 15 g/L compound peptone, 20 to 30 g/L yeast powder, 10 to 20 g/L dipotassium hydrogen phosphate, 1 to 5 g/L potassium dihydrogen phosphate, and 5 to 15 ml/L trace metal element, wherein the trace metal element comprises: 6 g/L ferrous sulfate, 0.35 g/L manganese sulfate monohydrate, 2.2 g/L zinc sulfate heptahydrate, 1.0 g/L anhydrous copper sulfate and 0.11 g/L ammonium molybdate, and wherein the compound peptone comprises tryptone and bovine bone peptone at a weight ratio of 2:1 to 3:1.

5. The method according to claim 3, wherein, in step (2), fermentation temperature is 36°° C. to 38° C., fermentation pressure is 0.03 MPa to 0.04 MPa, fermentation pH value is 6.8 to 7.0, and a first fermentation process occurs for 8 to 10 hours; then, the fermentation temperature is adjusted to 28° C. to 32° C., the fermentation pressure is adjusted to 0.05 MPa to 0.08 MPa, the fermentation pH value is adjusted to 7.2 to 7.6, and compound peptone, lactose and glucose are added in a second fermentation process; and the first fermentation process and the second fermentation process last for 100 hours to 130 hours at a stirring rate of 150 to 300 r/min.

6. The method according to claim 3, wherein, in step (3), concentration is carried out at a temperature lower than or equal to 70° C., and the fermentation broth is concentrated until a content of the solid is greater than 83%.

7. The method according to claim 3, wherein, in step (3), the crystallization with acetic acid is carried out at a constant temperature of 50° C., acetic acid is added at 0.5 to 3 times of a mass of a feed liquid, and crystallization lasts for 30 to 50 hours.

8. The method according to claim 3, wherein, in step (3), the solid obtained from centrifugation is subjected to dissolution, decolorization, ion-exchange, concentration and drying to obtain 2'-fucosyllactose powder, wherein the ion-exchange adopts full-bed ion-exchange with mixed cation and anion resins, wherein the cation and the anion resins are a D001 resin and a D301-F resin in a volume ratio of 100:110.

9. The method according to claim 3, wherein, the decolorization in step (3) is activated carbon decolorization at 50° C. to 60° C. and lasts for 50 minutes to 70 minutes, an amount of activated carbon is 3% to 5% of a dry matter content of the feed liquid, and a light transmittance of the feed liquid is greater than 85%,
wherein the ion-exchange in step (3) requires a feed temperature of 30° C. to 40° C., a flow speed of 2 to 3 BV/h, a discharge conductance lower than 50 uS/cm, and a discharge pH value is 3 to 6, and
wherein the concentration in step (3) is carried out at a temperature of 60° C. to 67° C. until the content of the solid is 50%; and
wherein the chromatographic separation in step (3) requires a mass concentration of chromatographic feed of 50%, a temperature of 60° C. to 63° C., and a ratio of water to material of 1:3 to 1:3.5.

* * * * *